United States Patent [19]
Wyatt et al.

[11] Patent Number: 5,597,728
[45] Date of Patent: Jan. 28, 1997

[54] METHODS FOR BIODEGRADATION SEPARATION OF NATURAL FIBERS TO RELEASE PARTICULATE CONTAMINATION

[76] Inventors: Caryl H. Wyatt; Bobby G. Wyatt, both of 3410 37th St., Lubbock, Tex. 79413

[21] Appl. No.: 319,072

[22] Filed: Oct. 11, 1994

Related U.S. Application Data

[63] Continuation-in-part of Ser. No. 96,615, Jul. 23, 1993, abandoned.

[51] Int. Cl.$^6$ .................. B09B 3/00; C12S 11/00
[52] U.S. Cl. .......... 435/262.5; 435/264; 435/821; 210/682; 210/691; 588/1; 588/20
[58] Field of Search ............... 435/262, 262.5, 435/263, 264, 267, 821, 277; 252/174.12; 8/408; 210/611, 922, 682, 691, 751; 588/1, 2, 9, 20; 536/127, 56, 20

[56] References Cited

U.S. PATENT DOCUMENTS

| | | | |
|---|---|---|---|
| 3,748,123 | 7/1973 | Bakker | 75/713 |
| 4,293,438 | 10/1981 | Ledebrink et al. | 588/6 |
| 5,427,247 | 6/1995 | Dugan et al. | 209/5 |

*Primary Examiner*—Carolyn Paden
*Attorney, Agent, or Firm*—Harris, Tucker & Hardin, P.C.

[57] ABSTRACT

A method is presented for releasing petroleum and hydrocarbon products sorbed onto or entrained by natural fibers in an aqueous medium through the use of enzymes to degrade the natural fiber sorbents utilized for oil spill cleanup, the method provides an opportunity for achieving responsible separation of oil from oil spill sorbent materials. Natural fibers which have been utilized to adsorb petroleum and hydrocarbon products are separated from these petroleum and hydrocarbon products by reducing the natural fiber links to the point that the adsorbed or entrained oil no longer has sufficient binding surface or fiber link to remain held by the fibers, thus float to the surface of the aqueous medium. Aqueous medium enzyme compositions are provided which are suitable for degrading natural fibers inclusive of cellulose-based and protein-based fibers resulting in release of adsorbed, absorbed and/or entrained radioactive contaminants.

13 Claims, No Drawings

METHODS FOR BIODEGRADATION SEPARATION OF NATURAL FIBERS TO RELEASE PARTICULATE CONTAMINATION

This application is a continuation-in-part of U.S. patent application Ser. No. 08/096,615, filed Jul. 23, 1993, now abandoned.

FIELD OF THE INVENTION

The present invention relates to aqueous medium enzyme compositions suitable for degrading natural fibers inclusive of cellulose-based and protein-based fibers and separating them from adsorbed, absorbed and/or entrained radioactive contamination materials. In another aspect the invention relates to a method of utilizing the aqueous medium enzyme compositions for removing adsorbed petroleum products, crude oil and other non-aqueous liquids from natural fibers which have adsorbent capabilities for these materials through biodegradation of the natural fibers.

Petroleum and hydrocarbon product spills produce an immediate and very observable impact on ecosystem. This impact can be minimized by appropriate rapid responses, ranging from controlled burning of, for example oil spills, to in situ bioremediation. Physical sorbents represent a direct approach to removal of spilled oil. These physical adsorbents can represent the primary removal method in the case of small spills, or adsorbents may serve to supplement mechanical equipment such as skimmers in the case of larger spills. Presently used physical adsorbents are not without problems regarding their usage, primarily the problem of reuse and/or disposal of petroleum or hydrocarbon product-soaked adsorbents.

Various chemicals have been used such as detergents and surface active agents to disperse oil spills. In most cases they only spread the spills over a larger area or allow them to sink into the water. Also, these chemicals are frequently pollutants which kill marine life. In most cases the chemicals are expensive and the oil cannot be salvaged for processing. Several oil adsorbing materials have been used such as straw or vermiculite to spread on the surface of the contaminated water where the oil leakage or spillage occurs. Saw dust is another particulate used in such oil spills on water, highways, drilling rigs, manufacturing areas and on the ground along beaches and coastal locations. These items have good adsorption advantages. However, when these materials are removed they ultimately become waste products and oil cannot be recovered.

Disposal of oil soaked adsorbents is frequently accomplished by placement in approved landfills, but this procedure is rather expensive and an economically undesirable approach. Approved incineration vastly reduces the amount of residual material associated with the disposal of used adsorbents, but such a process is also very expensive and may result in air pollution problems. Ideally, adsorbents would be reused on site and some adsorbents are fabricated or planned for reuse. Worn, reusable adsorbents must be properly disposed of and in the urgent context of spill clean-up, single use adsorbents are frequently more convenient. A recycling procedure has been suggested for a widely used adsorbent, airblown polypropylene fibers. These pads would be returned to the manufacturer for solvent extraction of hydrocarbons from the pads, then the airblown polypropylene fiber for example would be refabricated. In other procedures, for example non-woven fiber webs constructed of very short fibers of waste cotton, i.e. linters, gin motes and mill wastes, are utilized in providing recovery of spilled oil products; however, separation of the recovered oil products from the mat is by mechanical squeezing. U.S. Pat. No. 4,832,852 discloses use of a non-woven fiber mat for removing oil from a surface contaminated with the oil followed by separation of the oil from the mat by mechanical squeezing. U.S. Pat. No. 5,156,743 discloses a method for removing oil from the surface of a body of water using a layered sheet comprised of natural fibers to adsorb oil between the layers and the sheet, with the sheet later being removed from the water surface and compressed to squeeze oil from between the layers of the sheet.

Natural fibers are biodegradable and also possess a strong adsorbency for petroleum and hydrocarbon products and therefore should be considered for use as adsorbents at oil spill sites. Peat moss, saw dust, paper and paper waste products as well as cellulose fibers such as cotton and protein-based fibers such as wool and like are frequently used for this purpose. These natural fibrous materials may contain amounts of lignin or other compounds which are resistant to rapid biodegradation. Cotton fibers are essentially free of lignin and can be biodegraded. In contrast to processed cotton, raw cotton has considerable potential for selective removal of spilled oil and hydrocarbon products from surface waters, since the natural waxes on the raw cotton make it preferentially oil wet. This potential was recognized by Robert F. Johnson, et al. in an article entitled *"Removal of Oil from Prater Surfaces by Adsorption on Unstructured Fibers"*, Environmental Science & Technology, 7:439–443, 1973. However, biodegradation of natural fibers is generally undesirable. U.S. Pat. No. 5,120,463 specifically proportion cellulase multi-enzyme systems which are directed to detergent compositions useful as laundry detergents wherein said compositions possess excellent cleansing abilities while exhibiting reduced degradation potential against cotton fabrics.

Another disastrous disposal problem exists which is not necessarily the result of spills but from long-term manufacturing, laboratory experimentation and the like. This area of concern is the disposal of radioactive waste materials which exists in various levels of radioactivity strengths. The need for an effective means of reducing and storing radioactive waste has become increasingly apparent. Radioactive waste is currently produced and has been produced in significant quantities for the last five decades. For example, mill tailings alone can account for over twenty million tons of uranium-containing waste per year. Additionally, large volumes of previously produced but ineffectually treated waste are present throughout the world. In addition to these volumes of waste are the stored radioactive waste fabrics made from natural fibers such as laboratory clothing, towels and wipes. These products have been stored for many years in 55 gallon containers and impose a unique disposal problem aside from the disposal of direct mill tailings from uranium plants and high level of radioactive processed uranium cores. While these contaminated towels, wipes, laboratory clothing and the like, may represent different levels of radioactive contaminated materials, suitable methods for disposal have not been achieved.

The enzymatic modification of raw materials has been an important component of industrial processes for decades. However only recently has an increased understanding of molecular structure and function enabled workers to design processes which can utilize the enormous capability provided by naturally evolved catalytic systems, known as enzymes. Industrial applications are by no means equally distributed over the various classes of enzymes. Emphasis has been strongly biased toward hydrolytic enzymes, and more specifically toward peptide hydrolysis (the proteases). This biased leaning is a result of important industrial processes based on the action of intrinsic or exogenous hydrolytic activities. The bating (hair removal) of hides and leather production using the endogenous proteases and the natural saccharification of starch by amylases in alcoholic fermentations are two obvious examples. Also, the production of high fructose syrups by enzymatic action is a major industry.

Successfully creating industrial uses of enzymes is a more difficult task than it might appear. Two approaches require the identification of a process where existing enzymes might be utilized and improved or the finding of interesting or new enzymes followed by searching for a suitable advocation, both of these approaches require considerable experimentation and discovery.

Industrial use of enzymes presents multiple problems including costs, limited range of use regarding temperature, pH and the like as well as low solubility in aqueous solutions. However, enzymes can offer high or low specificity and can be selected to suit the desired bio function. Use of enzymes produce little or no byproduct formation and optimum activity occurs under very mild reaction conditions.

Enzyme specificity which can be a great advantage is also a disadvantage in the requirement for experimentation and discovery to determine specific enzyme combinations for specific biochemical outcomes. One enzyme, or perhaps one enzyme complex, catalyzes each biochemical reaction. Different enzymes possess specificities and it is possible to select an enzyme for a given process. Specificity not only reduces interference by undesirable substrates but minimizes the problems of unwanted byproducts.

The term "cellulase" refers to a multi-enzyme system which acts on crystalline and amorphous forms of cellulose and its derivatives to hydrolyze cellulose and give primary products, oligosaccharides, glucose and cellobiose. Cellulases are known in the art to be useful in detergent compositions, either for the purpose of enhancing the cleanability of the compositions or as a softening agents. Also, cellulases are used in fabric finishing operations where a soft feel or hand is desirable on the material. Cellulases in this application remove a portion of the fibers perpendicular to the surface of the cloth and produce a smoother fabric. However, regardless of its cleaning and/or softening mechanism, the use of cellulases in detergent compositions is complicated by the factor that exposure of cotton garments to cellulase results in partial degradation of the cotton fabric in these garments. Cellulases are known in the art as enzymes that hydrolyze cellulose (beta-1-4-glucan linkages) thereby resulting in the formation of glucose, cellobiose, and the like.

In view of the prior art efforts in using sorbents to soak up petroleum and hydrocarbon product spills, selectivity of the materials utilized and use and reuse of said materials, it is readily understood that such modem methods fail to address the total need of the environment as well as efficiency requirements when non-biodegradable sorbents are used to help clean up oil spilled on large water surfaces. Present systems utilize synthetic as well as natural fibers to adsorb the petroleum and hydrocarbon product materials from the surface of water or other sources. However, the separation of the petroleum and hydrocarbon materials from the synthetic and/or natural fibers is generally achieved by squeezing, thus leaving a residual petroleum/hydrocarbon content in the fibers which either must be burned or presented to a landfill. None of these prior systems suggest the use of enzymes for the release of petroleum hydrocarbons from natural fiber adsorbents used for oil spills. Accordingly, it would be highly desirable to provide an improved, ecologically sound method which utilizes simple and commonly available inexpensive natural fibers which do not require manufacturing of fabrics, sophisticated process equipment or utilizes other chemicals which can become contaminants to the environment as well.

Accordingly, it is an objective of this invention to develop enzymatic methods for the biodegradation of natural fiber sorbents and contaminant release of entrained or adsorbed petroleum/hydrocarbon materials for separation from the fibers. It is a further object of the invention to provide a method of removing oil from the surface of water utilizing sorbents that can be degraded in aqueous medium enzyme compositions. It is yet another object of the invention to provide a method of removing radioactive contamination from natural fibrous materials by degradation in aqueous medium enzyme compositions. These and other objects are achieved by the present invention as evidenced by the attached summary of the invention and detailed description of the invention and claims.

SUMMARY OF THE INVENTION

The present invention is directed to the discovery that use of enzyme compositions are suitable for releasing petroleum and hydrocarbon products sorbed on to or entrained by natural fibers in an aqueous medium. The use of enzymes to degrade the natural fibers sorbents used for aquatic oil spill clean-up provides a unique opportunity for achieving responsible separation of oil from oil spill adsorbent materials. Degradation of fibrous mats by enzymes contained in an aqueous medium releases the oil adsorbed to, or entrained in, the natural fibers by reducing fiber lengths to the point that the adsorbed oil no longer has sufficient binding surface or fiber length to remain held by the fibers and thus floats to the aqueous medium surface. The oil or hydrocarbon product can then be recovered from the aqueous medium surface using appropriate skimming and other methods. Efficiency separation rates by volume of 95–99% can be achieved as tested with diesel or light crude oils. The fibers undergo further degradation if allowed to remain in contact with the enzyme solution. Degradation of, for example, 90% by weight of cotton and cellulosic fibers has been obtained using cellulase as the enzyme. Residual material in this instance is comprised of cellulose, glucose and other non-degradable components of cotton. In addition, natural protein-based products such as wool and collagen or gelatin pads utilized as adsorbents for petroleum and hydrocarbon products can be separated from these contaminants in aqueous media utilizing proteases as the enzyme. However the process when degrading wool is enhanced through utilization of a reducing agent in order to break the disulfide cross linkages of wool.

In one method, the present invention is directed to a method for removing oil from the surface of water using sorbents and a method of removing oil from natural fiber adsorbents containing petroleum and hydrocarbon products through the utilization of various enzymes in an aqueous medium.

In another method, the present invention is directed to the release of radioactive particles and the like from fabrics made partially or totally from natural fibers of animal or vegetable origin. In this application, the use of enzymes to degrade fabrics made from natural fibers of animal or vegetable origin intentionally destroys the structure of the fabric. Depending upon the type of fibers in the fabric, the nature of the enzyme with which it is treated, and the conditions of treatment including but not limited to pH, time and temperature, the fabric is essentially dissolved completely, or extremely short fibers or fluff remain. In both instances, materials entrained in or on the fabric are released. The release may be complete, or residual material consisting of fiber and/or nonfibrous insoluble residues may still contain a portion of these entrained materials.

DETAILED DESCRIPTION OF THE INVENTION

Fiber has been defined as a relatively long, continuous piece of material made up of fine filaments. A fiber actually refers to a structure rather than a specific substance with the possibility of many substances combining to form the complicated matrix that we call fiber. The matrix can be comprised, for example of microfibrils of cellulose, a rigid glucose polymer. Hemicelluloses, pectins and other gums surround the cellulose as binding materials and in addition this matrix can be impregnated with lignin which can be visualized as a matrix in which the fibers are embedded. From this discussion of fibers, it is apparent that a single enzyme is not capable of totally hydrolyzing all the components of many natural fibers. In addition, the presence of many other components may hinder enzymes from reaching their substrate in the matrix. Frequently pretreatment methodologies such as grinding have been found necessary in order to achieve extensive hydrolysis of fiber components before effective enzyme treatment can be accomplished. Therefore, industry interest in the production and use of cellulolytic enzymes has been slow in developing probably because of the complexity of the cellulolytic enzyme system and the resistance of cellulose to rapid and efficient hydrolysis by enzymes and because of lack of cost-effectiveness.

Cellulose, one of many natural fibers, is probably the most abundant biological compound on earth and is found either in pure form (cotton) or in the form of lignified cellulose (wood) and can be found in more refined purity states such as in paper, fibers and textiles. Cellulose is the predominant waste material in agriculture in the form of stalks, stems, husks, gin trash and the like. Cellulose is a linear glucose polymer coupled by $\beta(1-4)$ bonds. Starch is a glucose polymer linked by $\alpha(1-4)$ bonds. Cellulose polymers can be very long and the number of glucose units in the cellulose molecule can vary from 15 to 15,000 with a mean value of about 3,000. Cellulose strands are usually coupled together by hydrogen bonds to give larger units. There remain different opinions about the number of cellulose molecules in such units and how they are organized. However it is thought that one area of the molecule will have regions of orderly configuration, rigid and inflexible in structure such as in crystalline cellulose and other regions of string-like flexibility in structure such as amorphous cellulose.

Cellulose fibers adsorb water and swell. The swelling is limited to the amorphous regions of the fiber. Strong hydrogen bonding network of the crystalline regions prohibit swelling. The number of bonds available for enzyme action will depend upon the degree of swelling of the cellulose, thus for sufficient hydrolysis of cellulose by cellulases, pretreatment to promote swelling is frequently necessary. Or in the alternative, reactions within an aqueous medium would promote such swelling and enhance enzymatic hydrolysis of the cellulose molecules. Cellulases are enzymes that degrade cellulose and are comprised of several different enzymes which are required to break down cellulose to glucose. In the breakdown of cellulose before pure glucose or relatively pure glucose is achieved, the fibers are reduced in length and size by degradation. These enzymes can attack cellulose through two modes. Endocellulases are capable of hydrolyzing the $\beta(1-4)$ bonds randomly along the cellulose chain and exocellulases cleave off glucose and/or cellobiose molecules from one end of the cellulose strand. These two modes of attack are also observed for amylases and proteases on their respective substrates. Enzyme preparations containing only endocellulases have little effect on native cellulose. On the other hand, those containing both endo- and exocellulases will cause significant degradation of cellulose. Thus the endo- and exocellulases work in a systematic and cooperative and/or synergistic manner on cellulose.

The hydrolysis product of simultaneous endo- and exocellulases activities are glucose, oligosaccharides and cellobiose, a disaccharide. As the cellobiose concentration increases in the reaction mix, exocellulase activity is inhibited. To obtain extensive cellulose hydrolysis, a procedure for removing cellobiose is needed. The enzyme cellobiase will achieve this by cleaving the cellobiose into two glucose molecules.

Cellulases, commercially available, generally include the following enzymes.

| | | |
|---|---|---|
| Systematic Name: | 1,4-β-D-Glucan glucanohydrolase | Endo-cellulase |
| Reaction Catalyzed: | It randomly hydrolyzes β (1–4) bonds in cellulose yielding oligosaccharides | |
| Source: | *Trichoderma reesei, T. viride, Aspergillus niger* | |
| Systematic Name: | 1,4-β-D-Glucan glucohydrolase | Exocellulase |
| Reaction Catalyzed: | It hydrolyzes β (1–4) bonds in β-glucans so as to remove successive glucose units, Hydrolyzes cellobiose slowly | |
| Source: | *Trichoderma reesei* | |
| Systematic Name: | 1,4-β-D-Glucan cellobiohydrolase | Exo-Cello-biohydrolase |
| Reaction Catalyzed: | It hydrolyzes β (1–4) bonds in cellulose to release cellobiose from the nonreducing ends of the chains | |
| Source: | *Trichoderma reesei, T. viride* | |
| Systematic Name: | β-D-Glucoside glucohydrolase | Cellobiase |
| Reaction Catalyzed: | It hydrolyzes the β (1–4) bond in cellobiose, giving two molecules of glucose | |
| Source: | *Aspergillus niger, T. Viride, S. cerevisae* | |

Another natural fiber, wool, that has neither been injured mechanically nor modified chemically is more resistant to attack by proteolytic enzymes such as pepsin, trypsin, chymotrypsin; however, papain and protease type IV were found to be effective. When the cuticle or scale layer of the fibers is damaged by mechanical means, the wool becomes much more susceptible to attack by pepsin and chymotrypsin. Under these conditions only a small portion of the wool is digested, yet the fibers are considerably weakened and their fiber structure is partially destroyed.

Most natural fibers, i.e. formed by natural means in nature versus fibers made from natural materials, can be categorized as proteins from animals such as wool; or cellulose from plants, such as cotton. When processed for use in textiles, these natural fibers become relatively easily wet by water, if they have been treated to remove surface oils and waxes; hence they are not highly suitable for selective adsorption of oil from an aquatic oil spill. Natural fibers must repel water to prevent water from soaking into the fiber and causing subsequent damage to the animal or plant. To fulfill this need, wool is mated with significant amounts of water repellent materials generally called lanolin. Similarly, unprocessed cotton fibers are coated with wax, which is a high molecular weight ester.

Cotton and wool with their surface waxes and oils still present appear to be natural fibers of choice for use as oil sorbents since the infrastructure for their large-scale growth, collection and marketing already exists. A typical price for apparel-grade wool is $1.30 per pound. An American Wool Council spokesperson estimated that 14 million pounds of wool which is unsuitable for apparel are available each year. This wool, whose fibers are too coarse and/or too short for apparel has a lesser value. Some of this poor quality wool is the result of raising lambs for meat, and keeping ewes for lamb production. Two forms of wool adsorbents were shown at the recent International Oil Spill Conference in Tampa. Wool adsorbent pads of weights varying from 6 to 12 ounces per yard were shown by Western Textile Products, and knopps, approximately ½ inch aggregates of wool developed in New Zealand were represented in the United States by Joymai Environmental.

A considerable amount of BG, below grade cotton, is produced as a result of early frosts and other adverse growing conditions. The amount produced in Texas alone varies from 2 to 85 million pounds per year. The potential for using cotton as an oil adsorbent was recognized in the late 70's at Texas Tech University, but the impetus for its actual use did not come until the recent increase in environmental awareness. At least one firm is producing cotton pads and booms for aquatic oil spills. Other natural fibers have been tested for use as oil spill sorbents, but these materials are not readily available at a low cost. These materials include milkweed, kenaf and kapok fibers.

Oil spill sorbents based on recycled newsprint, wood byproducts, and other plant materials are also available. For use with aquatic oil spills these materials may need to be made water repellent by special chemical treatments. These woody adsorbents generally contain significant amounts of lignin. Lignin degrades rather slowly, usually by fungi, hence the relative permanence of wood. For this reason, these lignin containing materials would be expected to biodegrade less rapidly and/or less completely than adsorbents made from relatively pure cellulose such as cotton, or protein such as wool.

Table 1 indicates the physical properties of a number of biodegradable adsorbents and polypropylene adsorbents. For purposes of this disclosure, the term adsorbed shall include absorbed and/or entrained. As would be expected all effective adsorbents have very large porosities, above 90%, so that a large quantity of oil can be retained relative to the weight of adsorbent used. The fiber diameters were uniform for cotton and wool due to their biological origin, whereas the diameters of the polypropylene fibers varied widely due to the method of manufacture. The air permeability and resulting calculated specific surface areas indicate that the polypropylene fibers are on the average finer than the natural fibers.

The oil-adsorbent capabilities, measured by the ASTM F726 procedure, are similar for all products tested except for raw cotton, whose capacity was considerably higher. These tests were made on a sweet West Texas Crude, whose initial API gravity was 33.3. Prior to testing the crude was weathered by blowing air through the crude oil until 30 weight percent of the crude had been vaporized. The resulting weathered crude oil had an API gravity of 23.8 and a viscosity of 73 cp. The oil capacities for two typical adsorbents using this crude oil at various stages of weathering indicate little change in adsorption capacity as a function of weathered viscosity. Cotton and wool perform effectively relative to polypropylene adsorbents.

In general, it can be observed that the natural fiber pads show similar performance capabilities to the polypropylene pads. It has been shown that unprocessed cotton is an effective adsorbent relative to polypropylene materials. Tests have shown the natural fiber pads including wool and cotton to be more effective than polypropylene pads. An oil capacity of 21.6 was reported for a 12 ounce wool pad compared to 12 to 17 grams heavy crude/gram of polypropylene adsorbent.

It should be stressed that these results are comparing commercial polypropylene pads, which presumably have been optimized for performance, with experimental cotton and wool pads whose adsorbent capacities have not yet been optimized. These results do clearly demonstrate that biodegradable pads made of either cotton or wool can perform effectively as adsorbents in comparison to commercial polypropylene products.

Disposal of oil-soaked natural fiber adsorbents using biological methods is possible because both the oil and the adsorbent are naturally occurring materials, and eventually will undergo biodegradation. Tasks in "developing" ex situ biologically based methods for the disposal of this material included finding ways to do it faster than the rate at which it would occur naturally in the environment, and developing a means for doing it under conditions where the material was confined and would not be released into any environmental sink. In addition, since two different materials had to be degraded, fiber and oil, another task was to determine whether degradation should be done sequentially, i.e. first degrade one, then degrade the other, or simultaneously.

In the interest of being able to better control and understand each process, it was decided that the best way to proceed would be to first find a way to degrade each substrate by itself, then to determine if each one could be degraded in the presence of the other. What is described below are some of the procedures we used to develop the technology for disposing of natural fiber sorbents with entrained hydrocarbons.

Adsorbents made of natural fibers (cotton or wool) are naturally biodegradable. They are broken down by microbial and/or enzymatic activity within a time frame of several weeks in a closed environment where optimum conditions for degradation can be provided and controlled. The structural integrity of the sorbents was degraded first releasing their entrained oil. This allowed the oil to be separated and recovered from the residual sorbent and the medium in which degradation occurred, for example, aqueous medium. Residue to be disposed of from this process include undegraded sorbent (generally 15% or less of the original amount) consisted of extremely short fibers which collectively form a "fluff" of material which has no collective structural integrity and the medium in which the adsorbent degradation occurred. As long as these residues do not contain hazardous levels of hydrocarbons, such residues can be disposed of as non-hazardous waste. The oil released from the adsorbent can be either recovered or degraded biologically. Recovery methods include those standard in the industry for separating petroleum hydrocarbons from aqueous media.

Table 1 presents various natural and man-made fibers frequently used as adsorbents.

TABLE 1

| Product | Shape and Thickness | Specification | Adsorbents Porosity | Permeability $(cm^2) \times 10^6$ | Fiber length (cm) | Fiber diameter (μm) | Specific surface area** $(cm^{-1})$ |
|---|---|---|---|---|---|---|---|
| Texas raw cotton | loose fiber, NM* | cellulose fiber | 0.99 | NM | 1.63 | 14 | NM |
| Cotton Pad | needle-punched sheet, ½" | cellulose fiber | 0.98 | 6.90 | 1.70 | 16 | 165 |
| Wool Pad | needle-punched sheet, ¼" | wool fiber | 0.95 | 8.43 | 2.69 | 24 | 143 |
| 3M HP156 polypropylene | sheet, ¼" | melt-blown fiber | 0.96 | 2.26 | NM | 0.5–36 | 280 |
| ERGON E100 | sheet, ⅜" | melt-blown fiber | 0.93 | 3.27 | NM | 3–10 | 222 |
| SPC 100 polypropylene | sheet, ⅜" | melt-blown fiber | 0.94 | 2.14 | NM | 0.85–9.4 | 279 |

*NM — not measurable
**calculated from Kozeny-Carman Equation:
$K = cP^3/S^2$ where K is permeability, P porosity, S specific surface area, c = 0.2

Wool fibers in which the disulfide cross-linkages have been broken, as by mechanical reduction, are almost completely digested by pepsin and chymotrypsin but are attacked only slightly by trypsin. Table 2 presents enzyme by type, supplier and degradation utilization suitable in accordance with the invention.

TABLE 2

| Enzyme | Type | Vendor | Separate |
|---|---|---|---|
| Rapidase ® | Cellulase | International Bio-Synthetics | Cellulose (raw cotton) |
| Indiage ® | Cellulase | Genecor | Cellulose (raw cotton) |
| Cellusoft ® | Cellulase | Novo Nordisk | Cellulose (raw cotton) |
| Protease: Type IV | Protease | Sigma Chem. Co. | Wool (raw, unscoured) |
| Papain | Protease | Spectrum Chemical Manufacturing Corp. | Wool (raw, unscoured) |
| Protease: Type IV | Protease | Sigma Chem. Co. | Collagen (formed pad) |

CELLULASES AND THEIR MANUFACTURERS

Enzyme: Rapidase ® GL
Manufacturer:   GIST-BROCADES, formerly
                INTERNATIONAL BIO-SYNTHETICS
                P. O. Box 241068
                Charlotte, NC 28224-1068
                (704) 527-9000
CAS Name: Cellulase
CAS Number: 9012-54-8
Product Code: 5299
Producing Organism: *Trichoderma reesei*
Activity: measured in carboxymethyl cellulase units (CCUs) = 98–106 CCU/gram liquid
Enzyme dosage recommended: 0.5–2.0%, O.W.G. (on weight of goods)
Enzyme: IndiAge ™ 44L
Manufacturer:   Genencor International
                4 Cambridge Place
                1870 South Winton Road
                Rochester, NY 14618
                (716) 256-5200
CAS Name: Cellulase
CAS Number: 9012-54-8
Product Code: CL601
Producing Organism: *Trichoderma reesei*
Activity: Activity: 2500 CMC units/ml*
Enzyme dosage recommended: For treating denim: a) 5–10 ml enzyme/kg denim if treated for 20–30 minutes, or b) 2.5–5 ml if treated for 30–45 minutes.
Enzyme: Denimax L
Manufacturer:   Novo Nordisk Bioindustrials, Inc.
                33 Turner Road
                P. O. Box 1907
                Danbury, CT 06813-1907
                (203) 790-2600
                Chemtrec Number: (800) 424-9300
CAS Name:
CAS Number: 9012-54-8
Producing Organism: *Trichoderma humicola isoenls*
Activity: Activity: measured in endoglucanase units (EGUs) = 90 EGU/gram
Enzyme dosage recommended:
Enzyme: Cellusoft L
Manufacturer:   Novo Nordisk Bioindustrials, Inc.
                33 Turner Road
                P. O. Box 1907
                Danbury, CT 06813-1907
                (203) 790-2600
                Chemtrec Number: (800) 424-9300
CAS Name: Cellulase
CAS Number:
Producing Organism: *Trichoderma reesei*
Activity: 750 EGU/gram (see Denimax for definition of EGU)
Enzyme dosage recommended: 0.5 to 2.0% on fabric weight
*Units are International Units (IU). 1 IU liberates 1 μmole reducing sugar (expressed as glucose equivalents) in 1 minute under standard conditions (50 C. at pH 4.8)

PROTEASES AND THEIR MANUFACTURERS

Enzyme: Protease, Type IV: Bacterial, purified
Manufacturer:   Sigma Chemical Company
                P. O. Box 14508
                St. Louis, MO 63178-9916
Producing Organism: *Streptomyces caespitosus*
Activity: 0.7–1.0 unit per mg solid*
Enzyme: Protease, Type V
Manufacturer:   Sigma Chemical Company
                P. O. Box 14508
                St. Louis, MO 63178-9916
Producing Organism: *Streptomyces griseus*
Activity: 0.7–1.0 unit per mg solid*
Note: This item was discontinued by the manufacturer in 1980. It is the same enzyme as Type XIV, differing from it in that Type V contained a starch extender.
Enzyme: Protease, Type VI (Pronase P)
Manufacturer:   Sigma Chemical Company
                P. O. Box 14508
                St. Louis, MO 63178-9916
Producing Organism: *Streptomyces griseus*

TABLE 2-continued

Activity: 3-4 units per mg solid*
Note: This item was discontinued by the manufacturer in 1980. It is the same enzyme as Type XIV, except it was referred to as a Pronase P (P grade) rather than as Pronase E.
Enzyme: Protease, Type XIV, Bacterial, (Pronase E)
Manufacturer: Sigma Chemical Company
P. O. Box 14508
St. Louis, MO 63178-9916
Producing Organism: *Streptomyces griseus*
Activity: approximately 4 units per mg solid*
Protease, unit definition:

One unit will hydrolyze casein to produce color equivalent to 1.0 μmole (181 μg) if tyrosine per min at pH 7.5 at 370 C. (color by Folin-Ciocalteu reagent), unless otherwise indicated.

Cotton is a filament of cellulose ready for use by the textile industry at a minimal price. It has been proposed recently to use cotton as a sorbent for oil spills. Due to cotton's physical properties, it accumulates oil readily and it is also a natural, biodegradable, non-polluting fiber. The present invention answers how to degrade the cotton in the easiest, quickest, and most complete manner possible using biological methods. Since attempting to degrade the oil soaked cotton as a whole is a difficult and complicated task, it is easier to try to degrade the oil and the cotton separately in order to have a general idea of what must be done to degrade the two as a whole and to determine which is the more effective way to do this. Thus an object of the invention was to determine the optimum conditions for degradation of cotton using enzymes in order to achieve quick and high efficiency release of sorbed oil.

Cellulase enzymes have been used for practical purposes in food processing and in the denim garment industry. They are used in the latter to improve the "hand" (or soft feel) of denim. Cellulase, in part, or entirely, replaces the "stone-washing" process. The tiny cotton fibers which stick up from the cloth when it is new are digested by the cellulase (or abraded away by the stones), thus making the fabric feel smooth. Once the cellulose molecules which comprise the surface fibers have been partially hydrolyzed, mechanical action then can remove the weakened surface fibers.

When cotton is treated with cellulase, there is a weight reduction and a loss in strength proportional to the amount of weight reduction. When the enzyme is first applied to the cotton, it begins to react with the cellulose fiber, partially hydrolyzing the molecules of cellulose. This occurs because the cellulase breaks the β-1, 4-glycosidic bonds of the cellulose molecule. Breaking the bonds by the hydrolytic chemical reaction catalyzed by cellulase removes glucose and cellobiose units from the cellulose molecule, making it smaller.

Cellulase enzymes generally are characterized by the pH range in which they are most effective. These categories include: acid stable, neutral stable, and alkaline stable. Cellulase degradation of cotton and oil soaked rags and papers generally used acid stable enzymes which perform best between pH values of about 3.5 to about 6.5.

In addition to pH, temperature is another critical factor which must be controlled. The temperature must be high enough for optimum enzyme activity, but low enough so that the enzyme does not denature. In order to optimize the cotton degradation, a proper ratio of time, temperature, pH, and amount of cellulase are required. Each of these parameters was tested experimentally to determine the optimum conditions for degrading the cellulose. Although most acid stable cellulase enzymes are most effective at temperatures of about 20° C. to about 60° C., a pH range of about 3.5 to about 6.5, and at concentrations of between about 50 to 100 ml enzyme solution per liter as supplied by the manufacturer, the amount degraded may vary depending on the enzyme source. Supplies of enzyme solutions provide technical procedures utilizing for example, cellulase, "On Weight of Goods (O.W.G.)" basis, volume of prepared enzyme solution to weight of goods (cotton) treated. According to the present invention, OWG of enzyme solution to natural fibers ranged from about 4 to about 30% (O.W.G.). Effective amounts of enzyme solution usage will vary depending on the natural fiber and/or specific enzymes. Thus, it was necessary to determine experimentally how each of these parameters affected the ability of various cellulase enzymes to degrade cotton. The goal was to degrade the maximum amount of cotton in the minimum amount of time.

Several commercial adsorbents including adsorbent pads made from wool and cotton, plus raw cotton have been tested for adsorption capacity, adsorption rate, and oil selectively. The tests generally followed the ASTM 726 procedure. In this procedure for adsorption capacity and adsorption rate, adsorbents are placed on the surface of oil contained in a shallow tray until visibly saturated and then drained for 30 seconds and weighed.

In the oil selectivity procedure, an absorbent pad, about 100×120 mm in size, is placed into a horizontal, 1-gallon jar, half full of water, and mechanically shaken at 150 cycles per minute for 30 minutes. Oil is added in 25 ml increments and shaken for an additional 30 minutes. The oil addition procedure is repeated until a layer of free oil remains on the water surface after shaking for 30 minutes, which implies saturation of the pad with oil. After draining for 2 minutes, the pad is weighed. The adsorbed liquid is extracted from pad with hexane, and water is separated from the hydrocarbons in a separatory funnel. The amount of oil adsorbed in the presence of water is obtained from total weight, dry pads weights and water weight.

The first series of tests employed 20 weight non-detergent motor oil as the test fluid. In general, the raw cotton showed significantly superior performance in all categories. It had approximately twice the adsorption capacity of next best material, Titan polyurethane pad, 60 versus 29 g oil/g adsorbent. The adsorption rate for raw cotton was only slightly higher than for other materials. In the presence of water, in the low rate oil exposure test, raw cotton was 50% better the next best material, a polypropylene pad, 3M-HP-156, 29 versus 20 g oil/g adsorbent. The raw cotton did not sink during the low rate oil exposure tests.

The Cotton Unlimited cotton pad containing polyester fibers did not perform as well as the raw cotton in these same tests. The performance was rather similar to the polypropylene pads. The Cotton Unlimited pad increased in volume and lost its shape, as the result of shaking and exposure to water during the low rate oil adsorption test. The wool pad performed similarly to the synthetics, except that it showed a higher rate of adsorption. It did not sink, and retained its integrity during the low rate oil adsorption test.

A similar series of tests have been performed using diesel fuel as the oil. The results are very similar to those results observed in the previous tests with 20 weight motor oil. Due to the viscosity difference, adsorption rates are much higher for diesel than for motor oil, and, in the presence of water, oil adsorption capacities for diesel are lower than for motor oil, since fluids are allowed to drain from the pad for 2 minutes prior to weighing. Most significant change is for raw cotton, which has an adsorption capacity for diesel that is only one-half of that for motor oil.

The following examples are offered to illustrate the present invention as well as comparative examples outside the invention. The comparative examples are offered in order to illustrate the refinements necessary in selecting variables such as pH, temperature, time, enzymes and the like to meet the requirements of the invention, i.e. the use of enzyme compositions in aqueous medium for the biodegradation of natural fibers which have been utilized for adsorbing petroleum product and hydrocarbon product spills. The first series of examples, Examples 1–9 are concerned with the degradation of cotton by Rapidase® cellulase without oil being adsorbed on the cotton. These examples illustrate the impact of varying pH, temperature and the like. Examples 10–11 present similar studies utilizing cotton having oils adsorbed thereon. Examples 12–15 are presented for showing the impact of utilizing a seawater aqueous medium on the process. Examples 16–18 presents studies reusing the enzyme both with and without oil. Examples 19–22 present studies for the degradation of cotton utilizing Indiage® cellulase with variations in specific parameters. Examples 23–28 present enzyme degradation of, for example, wool and cotton utilizing enzymes other than Rapidase® or Indiage®.

Experiments with Rapidase® (No Oils)

Example 1

Rapidase® (1 ml/75 ml medium) room temperature (RT) incubation, ca. 21°–22° C. 48 hr. incubation period Purpose: To test the ability of the commercial enzyme, Rapidase®, to degrade raw cotton and a commercially-available cotton pad (Cotton Unlimited, Post, Tex.).

Results:

| | % Cotton Degraded | |
| --- | --- | --- |
| | + Cellulase | − Cellulase |
| Raw cotton | 14 | 3 (both static and weathered) |
| CU pad | 16 | 3 (both static and weathered) |

Conclusions:
(1) More cotton was degraded in the presence of the Rapidase® enzyme than in its absence (true for both static and weathered [shaken] controls).
(2) There was no statistical difference in the amount degraded between the raw cotton and the Cotton Unlimited pad.

Example 2

Rapidase® (various concentrations) 32° C. pH 4.0

Purpose: To determine the optimum concentration of enzyme for maximum cotton degradation.

Results:

| Enzyme Concentration (mls & %) | % Cotton Degraded |
| --- | --- |
| 1 ml (1.33%) | 30 |
| 4 ml (5.06) | 40 |
| 8 ml (9.64) | 45 |
| 12 ml (13.79) | 43 (repeat = 41) |
| Static control | 3 |
| Shaken control | 0.5 |

Conclusions:
(1) Maximum degradation was obtained with 4 ml enzyme (approximately 5%).
(2) Increasing the amount of enzyme did not increase the amount of degradation under these conditions.

Example 3

Same set up as Example 2.

Purpose: To repeat Example 2 but extend the incubation period to 6 days (Example 2=3 days)

Results:

| Enzyme Concentration (mls & %) | % Cotton Degraded |
| --- | --- |
| 1 ml (1.33%) | 38 |
| 4 ml (5.06) | 63 |
| 8 ml (9.64) | 62 |
| 12 ml (13.79) | 59 |
| Static control | 1 |
| Shaken control | 2 |

Conclusions:
(1) Maximum degradation occurred at 4 and 8% concentration of enzyme.
(2) Extending the incubation period to six days from three increased degradation at all concentrations of enzyme (but not in the controls which lacked enzyme).

Example 4

Rapidase® (8 ml/75 ml medium) 32° C. incubation temperature 200 rpm vary pH

Purpose: To determine the effect of pH, and optimum pH, on cotton degradation.

Results:

| pH | % Cotton Degraded |
| --- | --- |
| 3.5 | 56 |
| 4.0 | 58 |
| 4.5 | 63 |
| 5.0 | 58 |
| 6.0 | 42 |
| 7.0 | 26 |

Conclusions:
(1) Maximum degradation under these conditions occurred at pH 4.5.
(2) Good degradation between pH 3.5 and 5.0; less at pH 6.0 and poor at 7.0.

Example 5

Same as Example 4 except:
(a) incubation extended to 6 days
(b) a "minus enzyme" control was done at each pH tested.

Purpose: To determine the effect of pH, and optimum pH, on cotton degradation to determine if low pH by itself leads to cotton degradation.

Results:

| pH | +/− enzyme | % Cotton Degraded |
|---|---|---|
| 3.5 | + | 53 |
|  | − | 2 |
| 4.0 | + | 56 |
|  | − | 1 |
| 4.5 | + | 66 |
|  | − | 1 |
| 5.0 | + | 65 |
|  | − | 1 |
| 6.0 | + | 47 |
|  | − | 2 |
| 7.0 | + | 24 |
|  | − | 2 |

Conclusions:
(1) Maximum degradation under these conditions occurred at pH 4.5 and 5.0.
(2) Good degradation between pH 3.5 and 5.0; less at pH 6.0 and poor at 7.0.
(3) No degradation in "minus enzyme" controls at each pH, thus pH alone does not affect degradation in the range tested.

Example 6

Rapidase® (8 ml) pH 4.5 (buffered) 200 rpm 6 day incubation period

Purpose: To determine the effect of temperature on cotton degradation.

Results:

| Temp °C. | +/− enzyme | % Cotton Degraded |
|---|---|---|
| 21–22 | + | 44 |
|  | − | 0 |
| 40 | + | 77 |
|  | − | 2 |
| 50 | + | 65 |
|  | − | 0 |
| 55 | + | 63 |
|  | − | 2 |
| 65 | + | 0 |
|  | − | 4 |

Conclusions:
(1) Maximum degradation under these conditions occurred at 40° C.
(2) Good degradation also at 50° and 55°; but enzyme inactive at 65° C.
(3) No degradation in "minus enzyme" controls at each temperature, thus temperature alone does not affect degradation.

Example 7

Rapidase® (4 ml) pH 4.5 (buffered) 40° C. incubation temperature 200 rpm vary incubation period: 3, 6, 9, 12 and 15 days Purpose: To determine the effect of time on cotton degradation.

Results:

| Incubation Time (days) |  | % Cotton Degraded |
|---|---|---|
| 3 | + enzyme | 50 |
| 6 | + | 67 |
| 9 | + | 76 |
| 12 | + | 80 |
| 15 | + | 90 |
| 15 | − enzyme | 3 |

Conclusions:
(1) Maximum degradation (90%) under these conditions occurred in 15 days.
(2) The longer the incubation period, the more cotton degraded.
(3) No degradation in "minus enzyme" control at the longest incubation time.

Example 8

Rapidase® (4 ml) pH 4.5 (buffered) 40 ° C. incubation temperature Either the medium was heated to 40° C. before adding the enzyme or it was not. Incubation was either static or shaking. Observations at 1, 2, 4, 6, 8, 24 and 48 hours after incubation beings. Results will be measured by loss of integrity of cotton mat (dissolution into fluffy bottom layer on flask or not)

Purpose: To determine:
(a) whether heating the solution to 40° C. before adding the enzyme hastens degradation.
(b) if agitation is needed for degradation or whether it will occur in static flasks.
(c) combination of (a) and (b).

Results:
(a) Static incubation: no degradation in 24 hr, and it did not make a difference whether the solution was heated before adding the enzyme or not.
(b) Shaking incubation:+degradation of mat in 24 hr, and it did not make a difference whether the solution was heated before adding the enzyme or not.

Conclusions:
(1) Heating the medium before adding the enzyme has no effect on cotton degradation (static or shaking incubation).
(2) Static incubation=no degradation, Shaking incubation=+complete degradation, as measured by loss of integrity of mat of cotton.

Example 9

Rapidase® (4 ml) pH 4.5 (buffered) 40° C. incubation temperature 200 rpm 3 or 6 days incubation Purpose: To determine if there is a difference in the amount of substrate degraded between raw cotton and the Cotton Unlimited pad.

Results:

| Substrate | Days incubation | % Cotton Degraded |
|---|---|---|
| raw cotton | 3 | 48 |
| " | 6 | 66 |
| CU pad | 3 | 41 |
| " | 6 | 59 |

Conclusions:
(1) Raw cotton and CU pad were degraded about the same amount after 3 days of incubation; after 6 days of incubation.
(2) More degradation occurred after 6 days as compared to 3 days.

Rapidase® Experiments (with Oils)

Example 10

Rapidase® (4 ml) pH 4.5 40° C. 200 rpm
Purpose: To determine if cotton can be degraded by the enzyme in the presence of diesel and crude oil (separately).
Results:

| Oil | Days | +/– enzyme | % Cotton Degraded |
|---|---|---|---|
| crude | 3 | + | 28 |
| diesel | 3 | + | 38 |
| none | 3 | + | 46 |
| crude | 6 | + | 64 |
| diesel | 6 | + | 65 |
| none | 6 | + | 60 |
| crude | 6 | – | 0 |
| diesel | 6 | – | 0 |

Conclusions:
(1) Cotton is degraded in the presence of either diesel or crude oil, and the oil is released and floats to the top of the flask.
(2) In the absence of the enzyme, cotton is not degraded and neither oil is released.

Example 11

Rapidase® (4 ml) 40° C. pH 4.5 200 rpm 5 ml diesel/0.5 g cotton or 5 ml crude oil/0.5 g time (hrs) varied: 3, 6, 24, 72
Purpose: To determine how quickly oil is released from the cotton in the enzyme solution.
Results:

| Time (hrs) | Oil | Results |
|---|---|---|
| 3 | crude | no degradation, no oil recovered |
|  | diesel | no degradation, no oil recovered |
| 6 | crude | no degradation, no oil recovered |
|  | diesel | no degradation, 0.1 ml diesel recovered |
| 24 & 72 | crude | degraded, oil recovered |
|  | diesel | degraded, oil recovered |

Conclusions:
(1) Degradation of the cotton by the enzyme sufficient to release the oils occurred between 6 and 24 hr.

Rapidase® Experiments with Seawater

Example 12

Rapidase® (4 ml) 40° C. pH 4.5 200 rpm ±Instant Ocean salts added to the medium to simulate seawater (9g/L, pH adjusted to 4.5 with HCl) Incubation for 3 or 6 days
Purpose: To determine if the enzymatic degradation of cotton is affected by the presence of the amount and kinds of salts normally found in seawater.
Results:

| Addition | Time (days) | % Cotton Degraded |
|---|---|---|
| Control (+ enzyme) | 3 | 48 |
| (McIlvaine buffer) | 6 | 69 |
| Control (no enzyme) | 3 | 0 |
| Instant Ocean | 6 | 0 |
| Experimental | 3 | 48 |
| (+ enzyme, | 6 | 68 |
| + Instant Ocean) | | |

Conclusions:
(1) Cotton degradation by enzyme was unaffected by the presence of seawater after either 3 or 6 days of incubation.
(2) No enzyme=no degradation.

Example 13

Same as Example 12 except that either 5 ml of diesel or crude oil was added to the cotton; no (–) enzyme controls were run.
Purpose: To determine if the enzymatic degradation of oil-soaked cotton is affected by the presence of the amount and kinds of salts normally found in seawater.
Results:
(a) no enzyme=no degradation or oil release
(b) other results varied with individual flasks and times; some released both diesel and crude after three days while others did not; same for 6 days.
(c) pH was adjusted with HCl; when checked at the end of the experiment in the flasks which had not released the oil; the pH was 5.3 to 6.0.

Example 14

Same as Example 13 except McIlvaine buffered Instant Ocean was used.
Results:

| Medium | Time (days) | % Cotton Degraded | ml Oil Recovered |
|---|---|---|---|
| Instant Ocean | 3 | 0 | 0 |
| (diesel) | 6 | 51 | 3.7 |
| Instant Ocean | 3 | 46* | 3.9 |
| (crude oil) | 6 | 49** | 3.5 |
| Control (no enzyme, | | | |
| + diesel | 6 | 0 | 0 |
| + crude) | 6 | 0 | 0 |

*only two of three underwent complete degradation and oil release (results based on these two flasks)
**only one of three underwent complete degradation and oil release (results based on only this one flask)

Conclusions:
(1) Rapidase® released oil (diesel or crude) from cotton in seawater.
(2) Release was delayed (up to 6 days or more, vs. 24 hr.)

Example 15

Rapidase® (4 ml) 40° C. pH 4.5 200 rpm Instant Ocean salts added to the medium to simulate seawater at concentrations ranging from 9% to 1%. No oil added. Diesel oil added; or crude oil added Incubation 6 days Purpose: To determine at what percentage of realistically occurring sea salts*, the release of hydrocarbons from and degradation of cotton is inhibited.

*"realistically occurring sea salts" means the concentration by weight which would be expected to occur in a pad which had been used to pick up oil from the ocean.

Results:

| % Sea Water | Oil | % Degradation |
| --- | --- | --- |
| 1% | none | 73 |
| 1% | diesel | 76 |
| 1% | crude | 75 |
| 0.5% | none | 74 |
| 0.5% | diesel | 74 |
| 0.5% | crude | 76 |
| 0.1% | none | 73 |
| 0.1% | diesel | 74 |
| 0.1% | crude | 74 |
| 0.01% | none | 75 |
| 0.01% | diesel | 72 |
| 0.01% | crude | 73 |
| 0% | none | 74 |
| 0% | diesel | 73 |
| 0% | crude | 73 |

Conclusions:
(1) There was release of oil and cotton degradation within 6 days for all the concentrations of sea salts tested. Sea salts at the levels that might be expected from raw cotton pads used to pick up oil on the ocean surface there would be no inhibition of oil release or cotton degradation.

Rapidase® Experiments (Re-use of the Enzymes)

Example 16

Rapidase® (4 ml) 40° C. pH 4.5 200 rpm Incubation for 3 days

Purpose: To determine if the enzymatic degradation of cotton (no added oil) can be accomplished by previously used enzyme solutions (not exposed to oils). Also, how does recovering the enzyme by filtration or centrifugation affect its activity as measured by the amount of cotton which remains at the end of the experiment (compared to new enzyme solution?)

Results:

| Medium | % Cotton Degraded |
| --- | --- |
| Filtered enzyme | 51 |
| Centrifuged enzyme | 52 |
| New enzyme (not used previously) | 56 |

Conclusions:
(1) Enzyme solutions previously used to degrade cotton are still active in degrading cotton alone (no oil added).
(2) Approximately 10% loss in activity vs. new enzyme solution.
(3) No difference in enzyme activity with regard to the method for collecting the used enzyme solution (filter vs. centrifuged).

Example 17

Rapidase® (4 ml) 40° C. pH 4.5 200 rpm Incubation for 3 days

Purpose: To determine if the enzymatic degradation of cotton (no added oil) can be accomplished by previously used enzyme solutions which had been exposed to oil (diesel or crude)

Results:

| Medium | Oil Exposure | % Cotton Degraded | % Activity Loss |
| --- | --- | --- | --- |
| Filtered enzyme | Diesel | 38 | 24 |
|  | Crude | 43 | 14 |
| New enzyme (not previously used) | None | 50 |  |

Conclusions:
(1) Enzyme solutions previously used to degrade oil-soaked cotton is still active in degrading cotton alone (no oil added).
(2) Some activity loss compared to new enzyme solution.

Example 18

Rapidase® (4 ml) 40° C. pH 4.5 200 rpm Incubation for 3 days New medium vs. medium recovered from Example 16 by either filtration or centrifugation Purpose: To determine if the enzymatic degradation of cotton (no added oil) can be accomplished by enzyme solutions previously used twice (not exposed to oils).

Results:

| Medium | % Cotton Degraded | % Loss of Activity |
| --- | --- | --- |
| Filtered enzyme | 34 | 26 |
| Centrifuged | 40 | 14 |
| New enzyme (not previously used) | 46 |  |

Conclusions:
(1) Enzyme solutions previously used to degrade cotton are still active in degrading cotton alone (no oil added).
(2) Some loss in activity vs. new enzyme solution.
(3) Some difference in enzyme activity with regard to the method for collecting the used enzyme solution (filtered lost more than centrifuged).

Experiments with Indiage®

Example 19

Indiage® (1, 4 or 8 ml/75 ml media) pH 5.0 (Mfg. recommended) 50° C. incubation (Mfg. recommendation, 50°–55° C.) 3 day incubation period Purpose: To test the ability of the commercial enzyme, Indiage®, to degrade raw cotton. Various concentrations of enzyme were tested.

Results:

| Enzyme Concentration (mls & %) | of Cotton Degraded |
| --- | --- |
| 1 ml (1.33%) | 38 |
| 4 ml (5.06) | 52 |
| 8 ml (9.64) | 51 |
| Shaken control | 2 |

Conclusions:
(1) Maximum degradation was obtained with 4 ml enzyme (approx. 5%).
(2) Increasing the amount of enzyme did not increase the amount of degradation under these conditions.
(3) Compared to Rapidase® at 3 days, Indiage® degraded more cotton at the 4 and 8 ml concentrations (Rapidase®=40 and 44% respectively).

Example 20

Same set up as Example 19.
Purpose: To repeat Example 19 but extend the incubation period to 6 days (Example 19=3 days).
Results:

| Enzyme Concentration (mls & %) | % Cotton Degraded |
| --- | --- |
| 1 ml (1.33%) | 45 |
| 4 ml (5.06) | 67 |
| 8 ml (9.64) | 65 |
| Control | 4 |

Conclusions:
(1) Maximum degradation occurred at 4 and 8% concentrations of enzyme.
(2) Extending the incubation period to 6 days from 3 increased degradation at all concentrations of enzyme (but not in the control which lacked enzyme).
(3) Compared to Rapidase® at 6 days, Indiage® degraded at about the same % cotton at the 4 and 8 ml concentrations (Rapidase® =63 and 62% respectively).

Example 21

Indiage® (4 ml/75 ml medium) 50°–55 ° C. incubation temperature 200 rpm vary pH 6 day incubation period
Purpose: To determine the effect of pH, and optimum pH, on cotton degradation in the presence of Indiage® enzyme. A control (minus enzyme) was run for each pH to ensure that degradation was not the result of pH alone.
Results:

| pH | +/−Enzyme | % Cotton Degraded |
| --- | --- | --- |
| 4.0 | + | 28 |
|  | − | 2 |
| 4.5 | + | 60 |
|  | − | 2 |
| 5.0 | + | 77 |
|  | − | 2 |
| 5.5 | + | 76 |
|  | − | 3 |
| 6.0 | + | 59 |
|  | − | 1 |

Conclusions:
(1) Maximum degradation under these conditions occurred at pH 5.0 and 5.5.
(2) Good degradation between pH 4.5 and 6.0; less at pH 4.0.
(3) No degradation in the absence of the enzyme, therefore, degradation not due to low pH.

Example 22

Indiage® (4 ml) pH 5.5 (buffered) 200 rpm 6 day incubation period
Purpose: To determine the effect of temperature on cotton degradation.
Results:

| Temp | +/−Enzyme | % Cotton Degraded |
| --- | --- | --- |
| 21–22 | + | 31 |
|  | − | 3 |
| 40 | + | 20 |
|  | − | 3 |
| 50 | + | 57 |
|  | − | 0 |
| 55 | + | 3 |
|  | − | 5 |
| 60 | + | 0 |
|  | − | 0 |

Conclusions:
(1) Maximum degradation under these conditions occurred at 50° C.
(2) Enzyme inactive at 55° C.
(3) At room temperature and 40 ° C., less than half the amount of cotton was degraded as at 50° C.
(4) No degradation in "minus enzyme" controls at each temperature, thus temperature alone does not affect degradation.
(5) Observation: enzyme appears to have a narrower temp. range than Rapidase®.

Enzyme Experiments (Other than with Rapidase® or Indiage®)

Example 23

Proteolytic enzymes: protease at pH 7.5 trypsin at pH 7.6 pepsin at pH 7.6 All enzyme solutions prepared in McIlvaine buffer Raw wool 37° C. for protease and pepsin; 25° C. for trypsin 200 rpm 3 days
Purpose: To determine if protein substrates such as raw wool and formed collagen can be degraded by proteolytic enzymes. Controls run without enzyme.
Results:

| Sorbent | Enzyme | % Sorbent Degraded |
| --- | --- | --- |
| wool | protease | 14 |
| wool | pepsin | 0 |
| wool | trypsin | 0 |

Note: As part of this experiment, formed collagen pads soaked with diesel fuel or crude oil also were tested to see if they would degrade in the protease. This was a "quick" experiment; oil release was all that was determined. Ans.= yes in 3 days at 37° C. in the protease solution.
Conclusions:
(1) Wool can be degraded slightly in 3 days by the protease, but not by trypsin or pepsin.
(2) Collagen pads were degraded by the protease and released the oils in three days.

Example 24

Proteases Crypes IV, V, VI and XIV) pH 7.5 buffered 37° C. incubation temperature 200 rpm 6 days Purpose: To determine if other proteases can degrade wool.

Results:

| Sorbent | Enzyme | % Sorbent Degraded |
| --- | --- | --- |
| wool | protease IV | 27 |
| wool | protease V | 18 |
| wool | protease VI | 20 |
| wool | protease XIV | 16 |

Conclusions:
(1) All were about as effective as the protease used in Example 23.
(2) A little more degradation after 6 days as compared to Example 23 (3 days).

Example 25

Papain (0.025%) with sodium bisulfite (2.0%) pH 6.5–7.5 (buffered) 65° C. incubation 200 rpm 1, 3, 6, 9, 12 days incubation raw wool Purpose: To determine if papain in the presence of sodium bisulfite degrades raw wool better than the proteases.

Results:

| Days incubation | % Wool Degraded |
| --- | --- |
| 1 | 93 |
| 3 | 90 |
| 6 | Dried |
| 9 | Dried |
| 12 | Dried |
| 3 control without enzyme but with sodium bisulfite = 10% degradation | |

Conclusions:
(1) Papain and sodium bisulfite successfully degraded wool.

Example 26

Denimax cellulase (5% tested—2%, mfg. recommended) pH 7 (pH 6–8 mfg. recommended) various temperatures (room temp., 45°, 50°, 55° and 60° C.—mfg. recommends 50°–60° C.) 200 rpm 6 days Purpose: To determine if another type of cellulase (Denimax) which runs at a higher pH can degrade raw cotton; if so, how much.

Results:

| Temp | +/−Enzyme | % Cotton Degraded |
| --- | --- | --- |
| room | + | 10 |
|  | − | 7 |
| 45 | + | 16 |
|  | − | 16 |
| 50 | + | 19 |
|  | − | 14 |
| 55 | + | 3 |
|  | − | 8 |
| 60 | + | 7 |
|  | − | 7 |

Conclusions:
(1) Under these conditions, this enzyme did not work well.

Example 27

Cellusoft® cellulase (5% test—2%, mfg. recommended) pH 7 (pH 4.5–5.5 mfg. recommended) various temperatures (room temp., 45°, 50°, 55° and 60° C.—mfg. recommends 45°–55° C.)

Purpose: To determine if another type of cellulase (Cellusoft®) which runs at a higher pH can degrade raw cotton; if so, how much.

Results:

| Temp | +/−Enzyme | % Cotton Degraded |
| --- | --- | --- |
| room | + | 0 |
|  | − | 2 |
| 50 | + | 20 |
|  | − | 1 |
| 55 | + | 0 |
|  | − | 1 |
| 60 | + | 0 |
|  | − | 1 |

Conclusions:
(1) Used wrong pH; mfg. recommended 4.5–5.5.
(2) Even under these conditions, got better degradation than the (minus enzyme) controls at 45° C.
(3) Experimental=controls at other temperatures.

Example 28

Rapidase® (4 ml) pH 4.5 40° C. 6 days incubation

Purpose: To determine if increasing agitation speed increases the amount of cotton degraded by Rapidase® in 6 days. A static control (no agitation, listed below as "0" rpm) was included.

Results:

| RPM | +/−Enzyme | % Cotton Degraded |
| --- | --- | --- |
| 0 | − | 4 |
| 0 | + | 38 |
| 50 | − | 2 |
| 50 | + | 39 |
| 100 | − | 3 |
| 100 | + | 53 |
| 200 | − | 1 |
| 200 | + | 60 |
| 250 | − | 1 |
| 250 | + | 64 |
| 300 | − | 0 |
| 300 | + | 63 |
| 350 | − | 0 |
| 350 | + | 67 |
| 400 | − | 0 |
| 400 | + | 66 |

Conclusions:
(1) No degradation in the absence of enzyme.
(2) No agitation (0 rpm) after 6 days led to measurable degradation (38%).
(3) 50 rpm was not better than no agitation (0 rpm).
(4) 100 to 400 rpm led to considerably more cotton degradation than 0 or 50 rpm.
(5) Slightly better cotton degradation at 200–400 rpm than at 100 rpm.
(6) No appreciable difference regarding the amount of cotton degraded between 200 and 400 rpm.

Example 28 agitation studies were conducted on a Lab Line Gyrotary (shaker) utilizing 125 ml flask mounted on a platform, rpm refers to platform rotation.

Examples 1–28 illustrate various refinements in accordance with the invention as compared to comparative examples which are outside the invention. Unexpected results were achieved in view of the prior art teachings, in Example 1, no statistical difference in the amount of degradation between raw cotton and a processed or a commercially available cotton pad was observed. Maximum degradation of cotton utilizing cellulase was found to occur in concentrations of the enzyme of between about 4 and 8% by volume of the reaction aqueous medium. Example 4 illustrates pH controls wherein good degradation was achieved between a pH of 3.5 and about 6.0 with less satisfactory results at a pH of 7.0. Cellulase degradation of cotton is found to provide maximum degradation in the aqueous solution at conditions of 40° C. with good degradation also at 50° and 55° C. Apparently enzyme activity ceases at temperatures of about 65° C. Diesel or crude oil adsorbed on cotton within the inventive aqueous medium utilizing cellulase was released and floats to the top of the container as the result of cotton degradation by the enzyme, as seen in the results of Example 10.

Example 11 utilizing various concentrations of enzymes provided time studies wherein the degradation of the cotton fibers was sufficient to allow the adsorbed oil to be released and recovered from the surface of the aqueous medium. Such timing occurred between about 2 hours and 24 hours. Under ideal conditions such as enzyme concentration, temperature of the aqueous medium and selection of enzymes, petroleum product release from the cotton fibers has been observed to occur at about 2 hours.

The process according to the invention was found to be of useful when the aqueous medium is comprised of seawater. In Example 28 impact of the additional enhancement variable, agitation of the aqueous medium containing the enzyme and the natural fiber which contains adsorbed petroleum products is shown. The enzymes utilized showed considerable tolerance to agitation, however enzyme activity may be impacted adversely by exaggerated shear forces.

Several examples address the concept of reusing enzyme solutions after said solutions were separated from the aqueous reaction medium on a continuous recycle methodology. Approximately 10% loss in activity was observed versus new enzyme solutions.

Cotton was degraded by the commercial enzyme, Indiage®, as compared to the commercial enzyme for cotton degradation Rapidase®. Both commercial preparations performed in accordance with the invention with similar results. Comparison of the various enzyme preparations, i.e. commercial preparations, indicate slight variations in pH, temperature and concentration refinements.

In the degradation of wool the enzyme protease is found to perform at a low concentration level for satisfactory degradation of the fiber. In Example 25 the enzyme papain in the presence of a reducing agent, sodium bisulfite, degrades wool at a very high level, for example, after one day of incubation, 93% wool degradation. Other methods of preparing wool fibers for enzyme degradation include mechanical milling and the like or the chemical reduction of wool fibers either before or simultaneously with the enzyme degradation processes.

The methodology for biodegradation separation of natural fibers and adsorbed petroleum products led to the present invention which is an alternative use of the technology and experimental data are presented which verify the application involving enzymatically treating fabrics made from similar organic natural fibers found in laboratory clothing, towels and wipes which have been contaminated by radioactive materials. These products have been stored for many years in 55 gallon containers and the problem of how to safely dispose of these materials and the associated radioactive contamination is of concern to the public and the federal government and is being addressed by both the Department of Defense and the Department of Energy.

The following two examples, Example 29 and Example 30 were performed to determine if a raw cotton fabric which was intentionally contaminated with a known amount of uranium compound (uranyl acetate, abbreviated UAc) releases the uranium upon enzymatic digestion with Rapidase® cellulase.

In Example 29 squares of fabric made of raw cotton were used. In the time allotted for enzyme treatment (6 days), not all of the fiber was digested. However, since all of the uranium salt initially was associated with the fabric, the results showed that the enzyme could release much of the uranium on the fabric into the liquid. In addition, uranium did not denature the enzyme at this concentration.

The utility of the information from Example 29 is that stored radioactive cotton-containing materials such as lab coats, lab wipers, etc., contaminated with uranium compounds can be treated with the enzyme solution to reduce the volume of contaminated material. Methods are available for disposal of radioactive materials in liquids, but methods are not available for disposing of contaminated laboratory clothing, etc. The present invention provides such a method in destroying the integrity of the material, resulting in a reduction in the volume of contaminated goods, and release of the radioactivity into the liquid medium for which disposal methods are available.

In Example 30, it was demonstrated that all the fiber can be digested by the enzyme solution. This resulted in the release of uranium salts into the liquid. Although uranium also was detected in the insoluble residue, the residue represented a very large volume reduction in comparison to the amount of the original fabric, and the residue was completely free of cotton fibers.

Methods for dealing with disposal of radioactive solids and liquids containing radioactive ions have been described. Two technologies relevant to the present invention process are vitrification (of solids, semi-solids and liquids) and ion scavenging from liquids.

Example 29

The fabric was prepared as a tube of jersey knit with 18s greige cotton yarn (=untreated raw cotton).

It was then treated with either TRITON X-100® or TRITON X-100® plus an aqueous solution of UAc. The TRITON X-100® was necessary to reduce the surface tension of the UAc solution so that the fabric could be wetted. Otherwise, since the fabric was made from raw cotton and is non-absorbent, the UAc solution would have beaded and rolled off the fabric.

Three samples of each fabric type were prepared, including:

(1) Control fabric (no TRITON X-100®, no UAc)

(2) Fabric with TRITON X-100® only (no UAc)

(3) Fabric treated with both TRITON X-100® and UAc.

The samples were weight 0.5 g each.

Each of the nine individual samples of fabric were placed into individual Erlenmeyer flasks (125 ml capacity) containing 71 ml McIlvaine buffer at pH 4.5 and 4 ml RAPIDASE®. The flasks were incubated at 40° C. for 6 days on a New Brunswick gyrotary shaker at 200 rpm.

At the termination of the incubation period, the flasks were removed from the shaker, and, individually, their contents were filtered through single pieces of Whatman #1 filter paper.

Aliquots of each filtrate were examined for uranium content, as was the undegraded residue from the enzyme-treated fabric samples captured on the filters.

Control fabrics (no enzyme treatment) also were analyzed for uranium content for comparative purposes.

The uranium contents of all of these samples is presented in the following table:

| Uranium Content, (Measured as Uranium, not Uranyl Acetate) | | | |
|---|---|---|---|
| Fabric Treatment | No Enzyme samples) | + Enzyme Treatment (residue from 0.5 g Treatment | Residual Enzyme |
| Untreated | 0.0001 mg/g U | 0.0018 mg U | 0.0136 mg/liter U |
| Blank Control [TRITON X-100 ®] | 0.0155 mg/g U | 0.0061 mg U | 0.0246 mg/liter U |
| Treated [TRITON X-100 ® with UAc] | 77.6 mg/g U | 25.9 mg U | 12.0 mg/liter U |

The results show that:

(a) a portion of the uranium remained with the non-degraded portion of the fabric treated with the enzymatic solution, and (b) some of the uranium was released into the enzyme solution.

Example 30

In this experiment, fabric prepared from raw cotton was treated with TRITON X-100® and uranyl acetate, as described in Example 29, with the following differences:

(1) 65.28 g fabric were treated with 11.62 g UAc.

(2) The TRITON X-100® control was omitted.

(3) UAc treated and untreated (control) fabrics were separately ground to powder using a Wiley mill. The fabric was ground to enhance both the total amount of degradation in the enzyme solution and the rate at which it underwent degradation.

(4) 5 g of the ground fabrics were removed for uranium analysis (these are the samples which did not receive any enzyme treatment).

(5) The powdered fabric which had been treated with uranyl acetate was placed in 12 liters of the enzyme solution in the air-lift reaction vessel.

Incubation was for 12 days at 45° C. until complete degradation of the fibers occurred, as determined by microscopic examination. Water was added as necessary to maintain the volume of the liquid.

At the termination of the experiment, the enzyme solution was turbid; microscopic examination revealed no residual fibers and no bacterial contamination.

The entire 12 liters of the enzyme solution was filtered. Undegraded material was collected on a filter and rinsed. (Note: Undegraded material is thought to consist of the waxes and insoluble materials associated with raw cotton.)

The insoluble residue, the used enzyme solution, and the water used to rinse the filter were assayed for uranium content. The uranium contents of both treated and control samples is presented in the following table:

| Fabric Treatment | No Enzyme Treatment | + Enzyme Treatment (insoluble residue) | Residual Enzyme |
|---|---|---|---|
| Untreated, ground raw cotton | 0.00136 g/g | Not Applicable | Not Applicable |
| Treated [TRITON X-100 ® with UAc] | 0.08 g/g | 0.159 g/g (rinse = 0.062 g/L) | 0.063 g/L |

The results show that:

(a) fabric made of raw cotton fibers intentionally contaminated with a soluble uranium salt can be completely degraded in the enzyme solution after being ground to a powder (b) uranium was detected in the insoluble residue (c) uranium was released into the enzyme solution (approximately the same amount of uranium was detected in the water used to rinse the insoluble material captured on the filter.

While various embodiments of the invention have been described using specific terms, and examples, such description is for illustrative purposes only, and it is to be understood that changes and variations may be made without departing from the spirit and scope of the following claims.

What is claimed is:

1. A method for separating radioactive contaminants adsorbed or entrained onto organic natural fibers, comprising:

admixing organic natural fibers containing radioactive contaminates with an effective amount of enzymes to degrade the organic natural fibers in an aqueous medium, said enzymes capable of degrading the fibers;

maintaining the admixture at a pH of from about 3.5 to about 8.0 and a temperature of from about 20° C. to about 60° C., as is sufficient to maintain the enzymes activity;

degrading the organic natural fibers by enzyme breakage of molecular chains constituting the fibers;

destroying the natural fiber integrity, fiber lengths sufficient for release of the radioactive contaminants;

removing the radioactive contaminants from the aqueous medium; and disposing of the aqueous medium and degraded fibers.

2. The method according to claim 1 for separating radioactive contaminants adsorbed or entrained on organic natural fibers wherein the aqueous medium admixture of organic natural fibers containing radioactive contaminants and enzymes are agitated for enhancing the degradation of the organic natural fibers.

3. The method according to claim 1 wherein the aqueous medium containing radioactive contaminates and enzymes are removed from a reaction chamber with the enzymes being reused for additive degradation of organic natural fibers, reused enzymes being made up to about 10% by volume of fresh enzyme solution introduction to the reaction mixture.

4. The method according to claim 1 wherein the enzyme concentration in the aqueous medium containing said fibers is from about 4% to about 30% on weight of goods.

5. The method according to claim 1 wherein the organic natural fibers are comprised of cellulose or modified cellulose materials and the enzymes are comprised of cellulases.

6. The method according to claim 5 wherein the cellulose or modified cellulose materials can contain up to about 40% by weight of man-made fibers or other organic natural fibers.

7. Method according to claim 1 wherein the radioactive contaminates are absorbed or entrained on organic natural fibers contained within fabrics constructed of said fibers.

8. A method for separating radioactive contaminants adsorbed or entrained on cellulosic fibers or modified cellulosic fibers, comprising:

admixing the cellulosic fibers containing radioactive contaminants with cellulases in sufficient concentration to degrade the cellulosic fibers in an aqueous medium;

maintaining the mixture at a pH of from about 4 to about 6.5 at a temperature of from about 20° C. to about 60° C., as is sufficient to maintain the cellulase activity;

agitating the aqueous medium containing the cellulases and cellulosic fibers containing the radioactive contaminants;

degrading the cellulosic fibers by breakage of cellulose molecule chains;

reducing cellulose chain links by destroying the β1-4 glycosidic bonds of cellulose thus reducing the length of the cotton fibers and releasing the radioactive contaminants;

separating the released radioactive contaminant in liquid form from the aqueous medium surface; and disposing of the degraded fibers, glucose, oligosaccharides, and the aqueous medium.

9. The method according to claim 8 wherein the fibers are substantially reduced to glucose and oligosaccharides in aqueous medium.

10. The method according to claim 9 wherein the released radioactive contaminants are separated from the aqueous medium by ion capture.

11. The method according to claim 9 wherein the released radioactive contaminants are separated from the aqueous medium by vitrification.

12. The method according to claim 8 wherein the enzyme concentration in the aqueous medium containing said fibers is from about 0.01% to about 0.025% and greater by weight to total volume.

13. The method according to claim 8 wherein the Cellulase concentration in the aqueous medium containing said fibers is from about 4% to about 30% on weight of goods.

* * * * *